(12) United States Patent
Stawiaski et al.

(10) Patent No.: US 10,089,744 B2
(45) Date of Patent: Oct. 2, 2018

(54) VESSEL SEGMENTATION

(71) Applicant: KONINKLIJKE PHILIPS N.V., Eindhoven (NL)

(72) Inventors: Jean Stawiaski, Paris (FR); Odile Bonnefous, Rueil-Malmaison (FR); Daniel Simon Anna Ruijters, Eindhoven (NL); Fred Simon Berend Van Nijnatten, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/782,210

(22) PCT Filed: Apr. 2, 2014

(86) PCT No.: PCT/IB2014/060371
§ 371 (c)(1),
(2) Date: Oct. 2, 2015

(87) PCT Pub. No.: WO2014/162273
PCT Pub. Date: Oct. 9, 2014

(65) Prior Publication Data
US 2016/0035103 A1 Feb. 4, 2016

(30) Foreign Application Priority Data
Apr. 3, 2013 (EP) .................... 13305426

(51) Int. Cl.
*G06T 7/20* (2017.01)
*A61B 6/00* (2006.01)
(Continued)

(52) U.S. Cl.
CPC ............. *G06T 7/20* (2013.01); *A61B 6/481* (2013.01); *A61B 6/504* (2013.01); *A61B 6/52* (2013.01);
(Continued)

(58) Field of Classification Search
None
See application file for complete search history.

(56) References Cited

U.S. PATENT DOCUMENTS 4,504,908 A * 3/1985 Riederer ............... A61B 6/481
128/922
7,450,743 B2 11/2008 Sundar et al.
(Continued)

FOREIGN PATENT DOCUMENTS

WO 2005073915 A2 8/2005
WO 2010018495 A1 2/2010

OTHER PUBLICATIONS

Waechter et al. "Using flow information to support 3D vessel reconstruction from rotational angiography," Med Phys. 35(7), Jul. 2008.*
(Continued)

*Primary Examiner* — Matthew Bella
*Assistant Examiner* — Soo Shin (57) ABSTRACT

An X-ray image processing device for providing segmentation information with reduced X-ray dose that includes an interface unit, and a data processing unit. The interface unit is configured to provide a sequence of time series angiographic 2D images of a vascular structure obtained after a contrast agent injection. The data processing unit is configured to determine an arrival time index of a predetermined characteristic related to the contrast agent injection for each of a plurality of determined pixels along the time series, and to compute a connectivity index for each of the plurality of the determined pixels based on the arrival time index. The data processing unit is configured to generate and provide segmentation data of the vascular structure from the plurality of the determined pixels, wherein the segmentation data is based on the connectivity index of the pixels.

15 Claims, 11 Drawing Sheets

(51) Int. Cl.
*G06T 7/11* (2017.01)
*G06T 7/174* (2017.01)
*G06T 7/187* (2017.01)

(52) U.S. Cl.
CPC ............... *G06T 7/11* (2017.01); *G06T 7/174* (2017.01); *G06T 7/187* (2017.01); *G06T 2207/10016* (2013.01); *G06T 2207/10116* (2013.01); *G06T 2207/30101* (2013.01); *G06T 2207/30104* (2013.01)

(56) References Cited

U.S. PATENT DOCUMENTS

| | | |
|---|---|---|
| 2003/0040669 A1 | 2/2003 | Grass et al. |
| 2006/0211940 A1 | 9/2006 | Antonelli |
| 2007/0098134 A1 | 5/2007 | Toyoshima et al. |
| 2007/0225606 A1* | 9/2007 | Naghavi ............ A61B 5/015 600/438 |
| 2009/0067568 A1 | 3/2009 | Hall et al. |
| 2009/0279752 A1 | 11/2009 | Sirohey et al. |
| 2010/0067767 A1 | 3/2010 | Arakita |
| 2010/0296623 A1* | 11/2010 | Mielekamp ............ A61B 6/032 378/4 |
| 2011/0170759 A1 | 7/2011 | Bjornerud et al. |
| 2013/0028494 A1 | 1/2013 | Groth et al. |
| 2013/0150766 A1* | 6/2013 | Olde ................... A61M 1/3653 604/4.01 |

OTHER PUBLICATIONS

Shpilfoygel et al. "X-ray videodensitometric methods for blood flow and velocity measurement: A critical review of literature," Med. Phys. 27(9), Sep. 2000.*

Alassi, "Estimating Blood Flow Based on 2D Angiographic Image Sequences," Master's thesis, Friedrich-Alexander Universität Erlangen-Nürnberg, Jan. 2012.*

Sepideh Alassi, Friedrich-Alexander-Universitat Erlangen-Nurnberg, "Estimating Blood Flow Based in 2D Angiographic Image Sequences", pp. 1-74

Wachter, Irina "3D Reconstruction of Cerebral Blood Flow and Vessel Morphology from X-Ray Rotational Angiography", 2009.

* cited by examiner

VESSEL SEGMENTATION

CROSS-REFERENCE TO PRIOR APPLICATIONS

This application is the U.S. National Phase application under 35 U.S.C. § 371 of International Application No. PCT/IB2014/060371, filed on Apr. 2, 2014, which claims the benefit of European Patent Application No. 13305426.2, filed on Apr. 3, 2013. These applications are hereby incorporated by reference herein.

FIELD OF THE INVENTION

The present invention relates to vessel segmentation, and relates in particular to a method for providing segmentation information, to an X-ray image processing device, and to an X-ray imaging system, as well as to a computer program element and a computer readable medium.

BACKGROUND OF THE INVENTION

In medical X-ray imaging, segmentation of vessels is used for providing enhanced information about a vessel structure, for example. Such information can be used for assessing a health state of a patient or also for planning of a necessary intervention, but also for live guidance during an intervention, and also for an evaluation of a treatment. For example, aneurisms are commonly treated endovascularily under guidance of live X-ray. Aneurisms can be treated by placing coils in the aneurism and/or stents in a feeding vessel. A further example is the placement of a flow diverter stent. For such treatment, knowledge about the blood flow inside the vessel is needed. For example, a three-dimensional radiographic angiography acquisition is made in order to assess the vasculature, its morphology, plan the procedure, and among others, also plan the optimal viewing angles for the flow acquisition. WO 2010/018495 A1 describes colour flow imaging in X-ray. However, it has been shown that an accurate segmentation, in particular for crossing vessels and aneurisms, improves measurements of the blood flow. An example for achieving segmentation information is the provision of at least two X-ray images from different angles to achieve the depth information. However, this means an additional X-ray dose and requires either that the X-ray system be moved, in which case the segmentation data cannot be obtained at the same time as the flow acquisition, or it requires the use of multiple X-ray imagers.

SUMMARY OF THE INVENTION

There may thus be a need to provide an improved and facilitated way of providing vascular flow and surrogate vessel geometry information with reduced X-ray dose.

The object of the present invention is solved by the subject-matter of the independent claims, wherein further embodiments are incorporated in the dependent claims. It should be noted that the following described aspects of the invention apply also for the X-ray image processing device, the X-ray imaging system and the method for providing segmentation information, as well as to the computer program element, and the computer readable medium. It is further noted that the following described aspects also apply for a method for operating a device, e.g. an image processing device, for providing segmentation information.

According to the present invention, an X-ray image processing device is provided, comprising an interface unit and a data processing unit. The interface unit is configured to provide a sequence of time series angiographic 2D images of a vascular structure obtained after a contrast agent injection. The data processing unit is configured to determine an arrival time index of a predetermined characteristic related to the contrast agent injection for each of a plurality of determined pixels along the time series. The data processing unit is further configured to compute a connectivity index for each of the plurality of the determined pixels based on the arrival time index. The data processing unit is further configured to generate segmentation data of the vascular structure from the plurality of the determined pixels, wherein the segmentation data is based on the connectivity index of the pixels. The data processing unit is further configured to provide the segmentation data for further purposes.

This provides the advantage that although only a 2D sequence of images is provided, depth information is provided nevertheless by taking into account the time factor related to the arrival of a contrast agent, for example, which then can be used for the segmentation data calculation. The sequence comprises only one 2D image for each point in time, thus meaning a minimum image dose exposure for the patient. The surrogate vessel geometry information is thus provided based on image acquisition with reduced X-ray dose, and only one geometry configuration, also facilitating the acquisition itself. Furthermore, since the segmentation data is derived from the same angiogram used for further purposes, there are no differences due to patient movement or vascular changes such as vasodilation that could occur when an extra acquisition is used for segmentation.

According to an example, the data processing unit is configured to compute a vessel confidence index for each of the plurality of the determined pixels, and to compute the connectivity index for each of the plurality of the determined pixels by combining the vessel confidence index with the arrival time index.

This provides the advantage that the vessel confidence index provides further detailed, and thus improved, information relating to the segmentation.

According to an example, the X-ray image processing device comprises a display unit, and the data processing unit is configured to generate a segmentation outline of the vascular structure from the segmentation data, and the display unit is configured to display the segmentation outline.

This provides the advantage in that the provision of the segmentation outline further improves the visible depth appearance, or in other words, further supports to provide three-dimensional information although the images, on which the presented displayed image is based on, only comprise 2D images and not 3D images.

According to the present invention, an X-ray imaging system is provided, comprising an X-ray imaging device and an image processing device. The X-ray imaging device is configured to generate a sequence of time series angiographic 2D images of a vascular structure. The X-ray image processing device is an X-ray image processing device according to one of the above mentioned examples.

According to an example, an injection device is provided, which is configured to controllably inject contrast agent into a vascular structure of an object during the acquisition of the sequence of time series 2D images.

For example, the object is a patient under observation, for example in a hospital. The provision of the injection device and a data and signal connection to the X-ray image processing device allows regulating the amount of contrast agent to be minimal.

According to the present invention, a method for providing segmentation information is provided, comprising the following steps:

a1) providing a sequence of time series angiographic 2D images of a vascular structure obtained after a contrast agent injection;

b1) determining an arrival time index of a predetermined characteristic related to the contrast agent injection for each of a plurality of determined pixels along the time series;

c) computing a connectivity index for each of the plurality of the determined pixels based on the arrival time index;

d) generating segmentation data of the vascular structure from the plurality of the determined pixels, wherein the segmentation data is based on the connectivity index of the pixels; and e) providing the segmentation data for further purposes.

According to an example, it is provided: b2) computing a vessel confidence index for each of the plurality of the determined pixels; and step c) comprises computing the connectivity index for each of the plurality of the determined pixels combining the vessel confidence index with the arrival time index. Step b2) can follow step b1), or vice versa; both steps b1) and b2) can also be provided simultaneously.

The segmentation of step d) is based on time connectivity. The segmentation is provided to segment the 2D flow sequence provided by the sequence of images.

In an example, step b1) comprises an analysis and/or characterization of key points, such as arrival time of contrast agent.

According to an example, following step a1), it is provided a step a2) comprising a time frequency analysis for providing a sequence of filtered images. Further, step b1) and/or step b2) are based on the filtered image.

In an example, one or both criteria are possible.

According to an example, for generating the segmentation data in step d), adjacent pixels are compared, and pixels are considered as connected if: i) a difference between the values of their contrast arrival time index is smaller than a predetermined threshold; and/or ii) the values of their vessel confidence index are higher than a predetermined threshold.

According to a further example, in step e), a segmentation outline of the vascular structure is generated from the segmentation data; and it is provided step f) displaying the segmentation outline.

According to an example, in step f), the segmentation outline is superposed onto a composite image generated from the vessel confidence index and the arrival time index of the pixels providing a contrast progression map to a user.

The term "contrast progression" relates to the provision of an intermediate contrast data analysis. The contrast progression can then be used for estimating flow in following steps of the processing, e.g. relating to flow velocity measurement. For example, the processing can provide flow information that can be shown as a flow information map.

According to an aspect of the present invention, the analysis of contrast arrival time is used for segmenting the image sequence; and the segmentation may be used in a 2D flow calculation, for example automatically. Thereby it is possible to calculate the connectivity per pixel, and therefore the invention allows separating and identifying false connections of crossing overlapping vessels or vessels touching each other in the X-ray image. The connectivity information can then be used as a mask in the flow extraction algorithm. The computation of a contrast arrival time map using an analysis of each pixel grey level along the time series, leads to an estimation of the arrival time of the contrast agent within each pixel of the whole image. In addition with a vessel confidence map, the quality of the arrival time map is further improved, leading to improved visual impression of the information for the user. This can then be used for segmentation, wherein the connectivity based on arrival time maps permits to distinguish different vessels that are superposed by projection. The identification of disconnected flow parts allows separately processing each non-overlapping segment and discarding vessel overlapping parts from the processing. It further allows identifying where specific processing techniques have to be used to extract flow field in the overlapping areas. The term "flow" relates to contrast displacement in the sequence, and thus to blood velocity.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
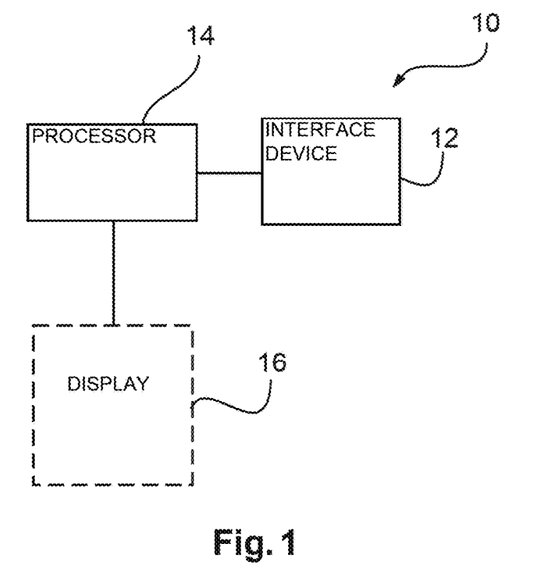
FIG. 1 schematically shows an example of an X-ray processing device.

FIG. 1 shows an X-ray image processing device 10, comprising an interface unit 12 and a data processing unit 14. The interface unit 12 is configured to provide a sequence of time series angiographic 2D images of a vascular structure obtained after a contrast agent injection. For example, the series of 2D images is provided by a (not shown) data base. In another example, the 2D images are provided by an X-ray imaging system (see also further below). The data processing unit 14 is configured to determine an arrival time index of a predetermined characteristic related to the contrast agent injection for each of a plurality of determined pixels along the time series. The data processing unit 14 is also configured to compute a connectivity index for each of the plurality of the determined pixels based on the arrival time index. The data processing unit is further configured to generate segmentation data of the vascular structure from the plurality of the determined pixels, wherein the segmentation data is based on the connectivity index of the pixels. The data processing unit 14 is further configured to provide the segmentation data for further purposes (not further shown in detail in FIG. 1).

In an example, a display unit 16 is provided, and the data processing unit 14 is configured to generate a segmentation outline of the vascular structure from the segmentation data, and the display 16 is configured to display the segmentation outline. It is noted that the provision of the display unit 16 is shown as an option in FIG. 1, as indicated by the dotted lines.

Figure 2:
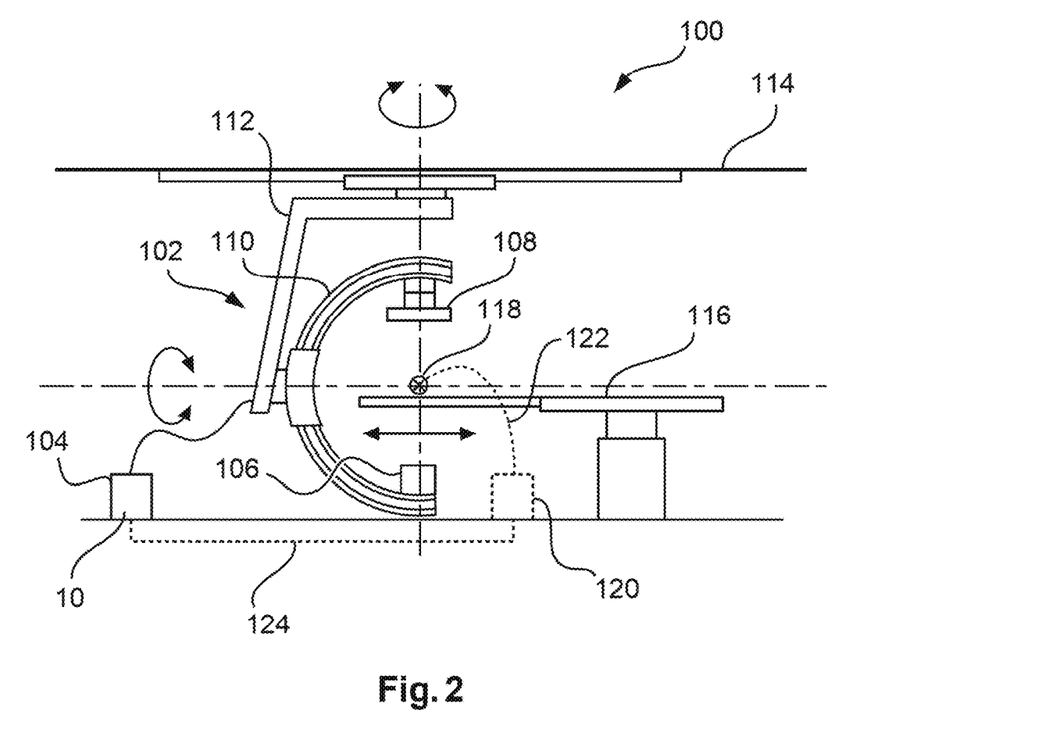
FIG. 2 schematically shows an example for an X-ray imaging system in elevation.

FIG. 2 shows an X-ray imaging system 100 comprising an X-ray imaging device 102 and an image processing device 104. The X-ray imaging device 102 is configured to generate a sequence of time series angiographic 2D images of a vascular structure. The X-ray image processing device 104 is an X-ray image processing device 10 according to one of the above mentioned examples. For example, the X-ray imaging device 102 may be provided as a C-arm system, where an X-ray source 106 and an X-ray detector 108 are arranged on opposing ends of a movable C-arm structure 110. The C-arm structure 110 may be supported by a movable support 112, for example suspended from a ceiling 114. Further, an object receiving device 116, for example a patient table, is provided. An object, indicated with a circle 118, may be provided on the patient table 116, and 2D images can be acquired by the X-ray imaging device 102. Also other X-ray imaging arrangements are provided, such as a CT system or a fixed X-ray system.

In an example, an injection device 120 is provided that is configured to controllably inject contrast agent into a vascular structure of the object 118 during the acquisition of the sequence of time series 2D images. It is noted that an arrangement for injecting the contrast agent is shown by a simple dotted line 122. Further, another dotted line 124 indicates a data connection with the image processing device 104. It must be noted that the injection device 120 is shown as an option in FIG. 2, which is also indicated by using respective dotted lines.

Figure 3:
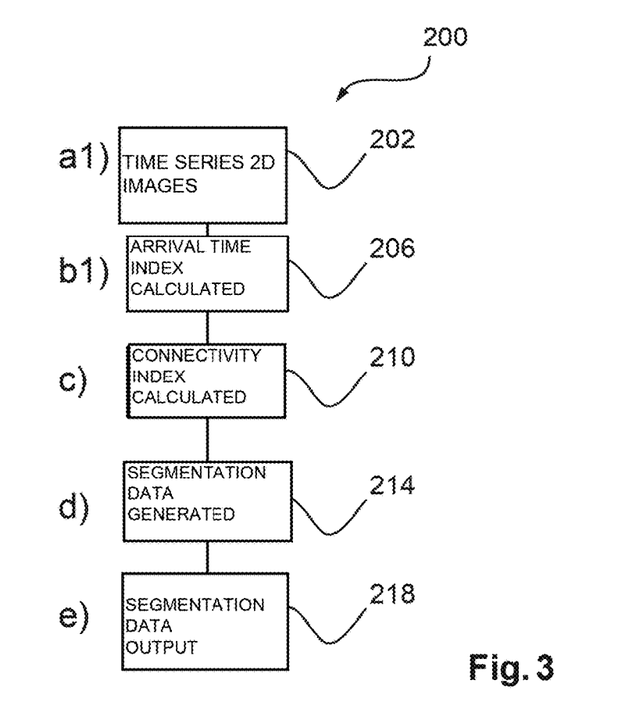
FIG. 3 shows basic steps of an example of a method for providing segmentation information that can be used for achieving vascular flow information.

FIG. 3 shows a method 200 for providing segmentation information, comprising the following steps: In a first step 202, a sequence 204 of time series angiographic 2D images of a vascular structure obtained after a contrast agent injection is provided. In a second step 206, an arrival time index 208 of a predetermined characteristic related to the contrast agent injection is determined for each of a plurality of determined pixels along the time series. In a third step 210, a connectivity index 212 for each of the plurality of the determined pixels is computed based on the arrival time index. In a fourth step 214, segmentation data 216 of the vascular structure is generated from the plurality of the determined pixels, wherein the segmentation data 216 is based on the connectivity index 212 of the pixels. In a fifth step 218, the segmentation data 216 is provided for further purposes. The first step 202 is also referred to as step a1), the second step 206 as step b1), the third step 210 as step c), the fourth step 214 as step d), and the fifth step 218 as step e).

Figure 4:
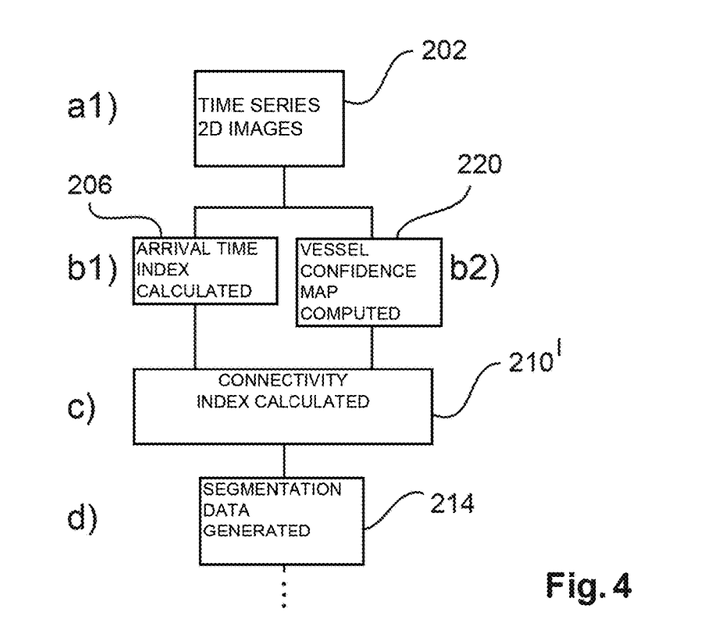
FIGS. 4 to 8 show further examples of a method for providing segmentation information.

In a further example, shown in FIG. 4, a computing step 220 is provided, for computing a vessel confidence index 222 for each of the plurality of the determined pixels. The computing step 220 may be provided parallel to the second step 206. The computing step 220 is also referred to as step b2). Further, step c) comprises computing the connectivity index for each of the plurality of the determined pixels combining the vessel confidence index 222 with the arrival time index 208. This enhanced computing of step c) is indicated with reference numeral 210', and the resulting connectivity index, also referred to as an enhanced connectivity index due to using the combination of the vessel confidence index with the arrival time index, is indicated with reference numeral 212'.

In step b1), the predetermined characteristic may be provided as arrival time of contrast agent, time to peak of contrast agent, time for contrast fading or a wash-out-time, or time for minimum contrast agent. The predetermined pixels may be all pixels or a selected region of the image. In an example, step b1) comprises computing an arrival time map. In another example, step b2) comprises computing a vessel confidence map.

Figure 5:
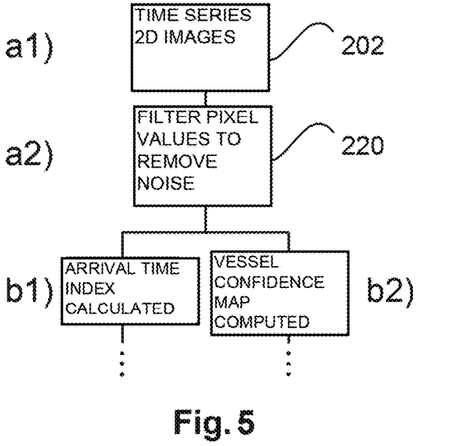

FIG. 5 shows a further example, in which following step a1), a further step 220 is provided where a time frequency analysis for providing a sequence of filtered images 222 is performed. Following, steps b1) and/or b2) are based on the filtered images 222.

In one example, step b1) of determining an arrival time index of a predetermined characteristic related to the contrast agent injection for each of a plurality of determined pixels along the time series is based on a sequence of filtered images 222.

In a further example, step b1) of determining an arrival time index of a predetermined characteristic related to the contrast agent injection for each of a plurality of determined pixels along the time series is based on the sequence of filtered images, and step b2) of computing a vessel confidence index for each of the plurality of the determined pixels is also based on the sequence of filtered images 222. In one example, step a2) comprises filtering pixel values of the sequence of angiographic images to remove noise.

Figure 6:
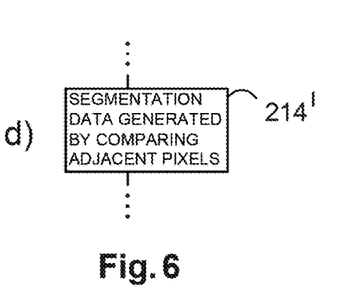

In a further example, indicated in FIG. 6, for generating the segmentation data in step d), adjacent pixels are compared in a comparison step, indicated with reference numeral 214', and pixels are considered as connected if one or both of the following applies: as a first criteria, the difference between the values of their contrast arrival time index is smaller than a predetermined threshold. As a second criterion, alternatively or additionally applied, the values of their vessel confidence index are higher than a predetermined threshold.

In one example, for generating the segmentation data in step d), adjacent pixels are compared, and pixels are considered as connected if a difference between the values of their contrast arrival time index is smaller than a predetermined threshold.

In another example, for generating the segmentation data in step d), adjacent pixels are compared, and pixels are considered as connected if a difference between the values of their contrast arrival time index is smaller than a predetermined threshold, and if the values of their vessel confidence index are higher than a predetermined threshold.

Figure 7:
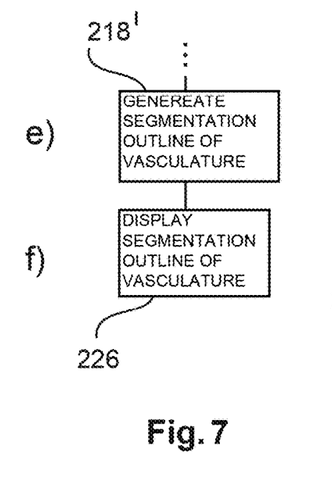

FIG. 7 shows a further example, where a segmentation outline 224 of the vascular structure is generated from the segmentation data, which generation procedure is indicated with reference numeral 218'. It is further provided a display step 226, also referred to as step f), for displaying the segmentation outline 224.

In an example, the segmentation outline 224 is superposed or combined with: f1) a vessel confidence map generated based on the vessel confidence index of the pixels; and/or f2) an arrival time map generated based on the arrival time index of the pixels.

Figure 8:
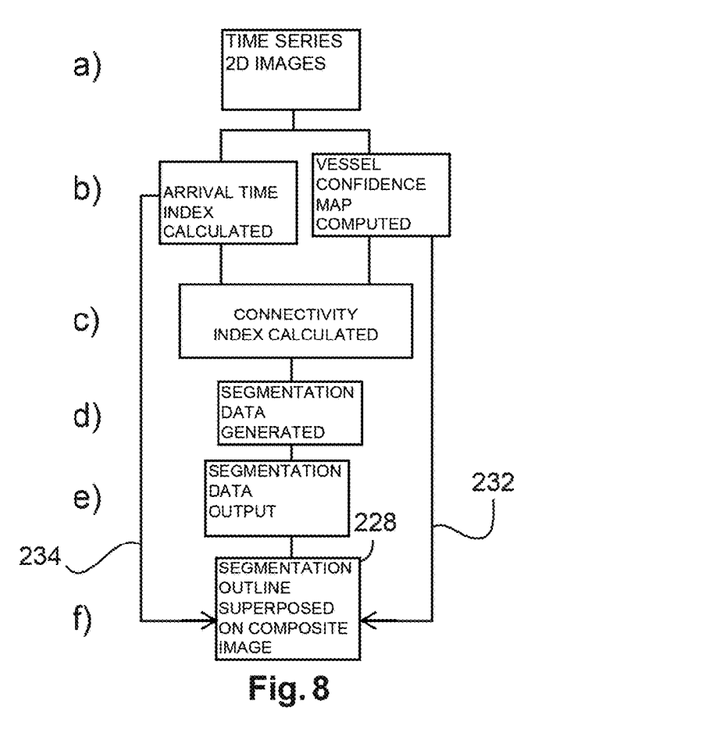

FIG. 8 shows an example, in which in step f) the segmentation outline 224 is superposed, indicated with reference numeral 228, onto a composite image generated from the vessel confidence index 222 and the arrival time index 208 of the pixels, providing a contrast progression map 230 to a user. The use of the data of the vessel confidence index 222 and the arrival time index 208 is indicated by two arrows 232, 234, symbolically indicating the entering of the respective data into step f).

It is noted that in a further example, only one of the above-mentioned vessel confidence index and the arrival time index is used for the composite image forming the contrast progression map.

The contrast progression map 230 may comprise a first graphical parameter indicating the arrival time and a second graphical parameter indicating the confidence. For example, the graphical parameter is a colour code and the second graphical parameter is saturation of a transparency grade.

According to a further example, not further shown, for overlapping vessels, at least two arrival time indices (values) are determined. Further, at least two connectivity indices (values) are determined and stored separately.

According to a further example, also not further shown, following step d), it is provided to use the connectivity information comprised in the segmentation data as a mask in a following flow algorithm for determining blood flow information.

The term "mask" refers to determining boundary lines in the pixels for separating parts of the pixels from other parts. From the knowledge of the connectivity indices and the confidence map, several vessel segments with no overlapping are defined. A label is attached for each segment. A composite mask image is obtained where each label value corresponds to a particular vessel segment map. For each label (or segment), the flow field is extracted separately, allowing to get disconnected flow fields from disconnected vessel segments. This allows also discarding regions with overlapping vessels from the flow processing. The flow processing part itself may be provided as known in the art. According to the present invention, the mask is provided as an input of the flow processing steps.

According to a further example, connectivity of overlapping vessels, calculated from at least two arrival time indices, is stored separately and a multilayer mask is provided to a following flow algorithm, so that for each layer the blood flow information can be calculated separately.

According to a further example, connectivity of vessels is determined for multiple time moments, at least two, based on the calculation of at least two arrival time indices for overlapping vessels. The multiple connectivity indices can be used by the following flow algorithm to process parts of the image sequence using a different connectivity index. This could be beneficial in the case of a relative short contrast injection or long image sequence, where vessels do not overlap during the full image sequence.

Further, it is also provided a method for operating a device for providing segmentation information, comprising the following steps: a1) providing a sequence of time series angiographic 2D images of a vascular structure obtained after a contrast agent injection to a processing unit; b1) determining an arrival time index of a predetermined characteristic related to the contrast agent injection for each of a plurality of determined pixels along the time series by the processing unit; b2) computing a vessel confidence index for each of the plurality of the determined pixels by the processing unit; c) computing a connectivity index for each of the plurality of the determined pixels by combining the vessel confidence index with the arrival time index; d) generating segmentation data of the vascular structure from the plurality of the determined pixels by the processing unit, wherein the segmentation data is based on the connectivity index of the pixels; and e) providing the segmentation data for further purposes.

It is in particular noted that the method for operating a device is relating to operating an image processing device. The method steps are based on a sequence of images that, for example, may be provided by a data base where the date is stored. Relating to the method of operating the device of the image processing device, the injection of contrast agent is not part of the method steps, but rather only performed for the acquisition of the images. However, the acquired images may be images required also for other purposes, as long as the time series provides a relation of the particular image with the particular time index for determining the visual appearance of the contrast agent while being injected.

According to the present invention, it is proposed to compute a contrast arrival time map using an analysis of each pixel grey level along the time series. This permits to estimate the arrival time of the contrast agent within each pixel of the whole image. Alternatively, also other features of the contrast arrival time map can be used to reach the same objectives, e.g. time to peak, time that contrast washes out, etc. On the other hand, to suppress the sometimes troublesome visual impression of the computed arrival time map, it is provided to use a vessel confidence map to correct and enhance the quality of the arrival time map. This technique leads to the generation of a colour coded image, where the colour indicates the arrival time and the saturation indicates the confidence within the displayed value. With this technique, a maximum of information in a single image is summarized and superposed and occluded vessels are accurately visualized. This image is then segmented, for example using a method as region growing within a certain confidence range. The connectivity based on arrival time maps permits to distinguish different vessels that are superposed by projection.

Figure 9:
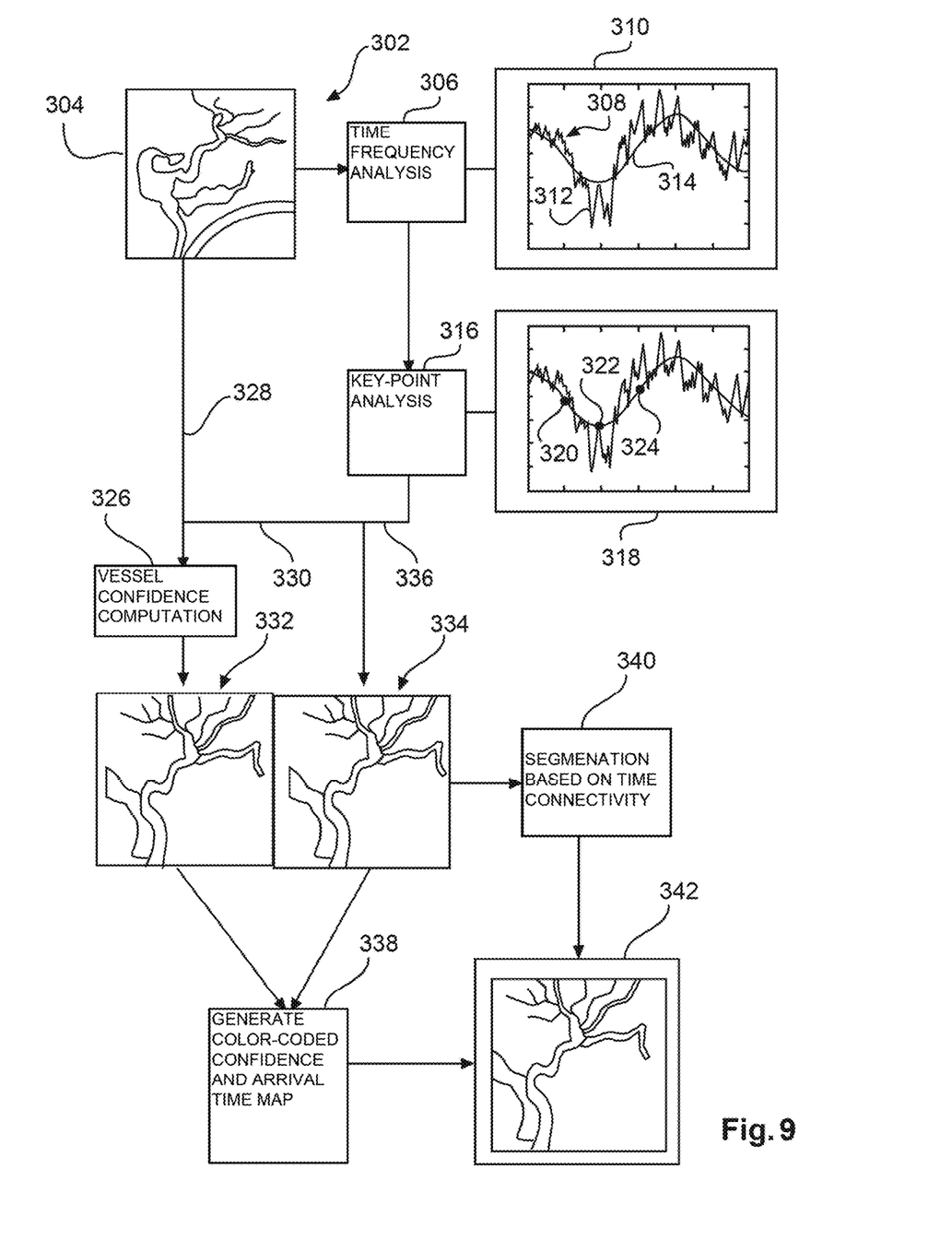
FIG. 9 shows a further example of a method for providing segmentation information.

FIG. 9 shows a further example of method steps:

As indicated, a real-time sequence 302 of angiography obtained after a contrast agent injection within an artery is provided as an input 304.

Further, a time frequency analysis 306 may be provided. A graph 308 in a further frame 310 indicates a graph of original time series 312 and a resulting filtered time series 314. In the time frequency analysis 306, each pixel grey level time variation may be filtered in order to remove noise and to compute the arrival time of the contrast agent. This filtering process can rely on different technologies, such as adaptive recursive time filter, Wiener filter, Fourier transform, or discrete Cosine transform. The aim of this process is to remove noise and contrast agent variation due to blood flow pulsatility.

In a next step 316, key-points analysis and characterization is provided. For example, a further frame 318 indicates an arrival time 320, a minimum contrast time 322, and a wash-out-time 324, as possible key points along the graph. For example, the filtered time series are interpreted according to a general model of contrast injection containing a time of contrast arrival, a time where the contrast is flowing out, and a time of maximum contrast presence. These key points are found automatically and respectively defined as: i) the time, where the gradient of the time series is minimal; ii) the time, where the gradient of the time series is maximal and greater than the previously defined arrival time point; iii) the time, where the time series is minimal and between the two previously described points.

As a further step, a vessel confidence computation 326 is provided. The vessel confidence computation 326 may either be supplied with the angiography sequence 302, as indicated with arrow segment 328, or by the filtered an analyzed data, as indicated with arrow segment 330. Below the vessel confidence computation step 326, a vessel confidence map 332 is shown.

Further, a contrast arrival time map 334 may be generated, for example based on the results from the key points analysis and characterization step 316, as indicated with line arrow segment 336. It is further also possible to use the angiography sequence 302 for building the graphical representation of the contrast arrival time map, for example for indicating anatomical surroundings.

As a further step, a step of generating 338 a colour-coded confidence and arrival time map is provided. The final colour-coded image may be build such that the colour indicates the arrival time and saturation indicates the confidence within the displayed value. The colour-coded image can also be equivalently generated from a collared arrival time map, where the alpha transparency of each pixel is controlled from the vessels confidence map.

Further, a segmentation step 340, based on time connectivity is provided. Pixels are considered as connected if the difference between their contrast arrival time values is smaller than the given threshold $t_1$ and their vessel confidence are higher than a threshold $v_1$. The segmentation can then be used together with the colour coded confidence and arrival time map to generate a contrast progression map 342.

Figure 10:
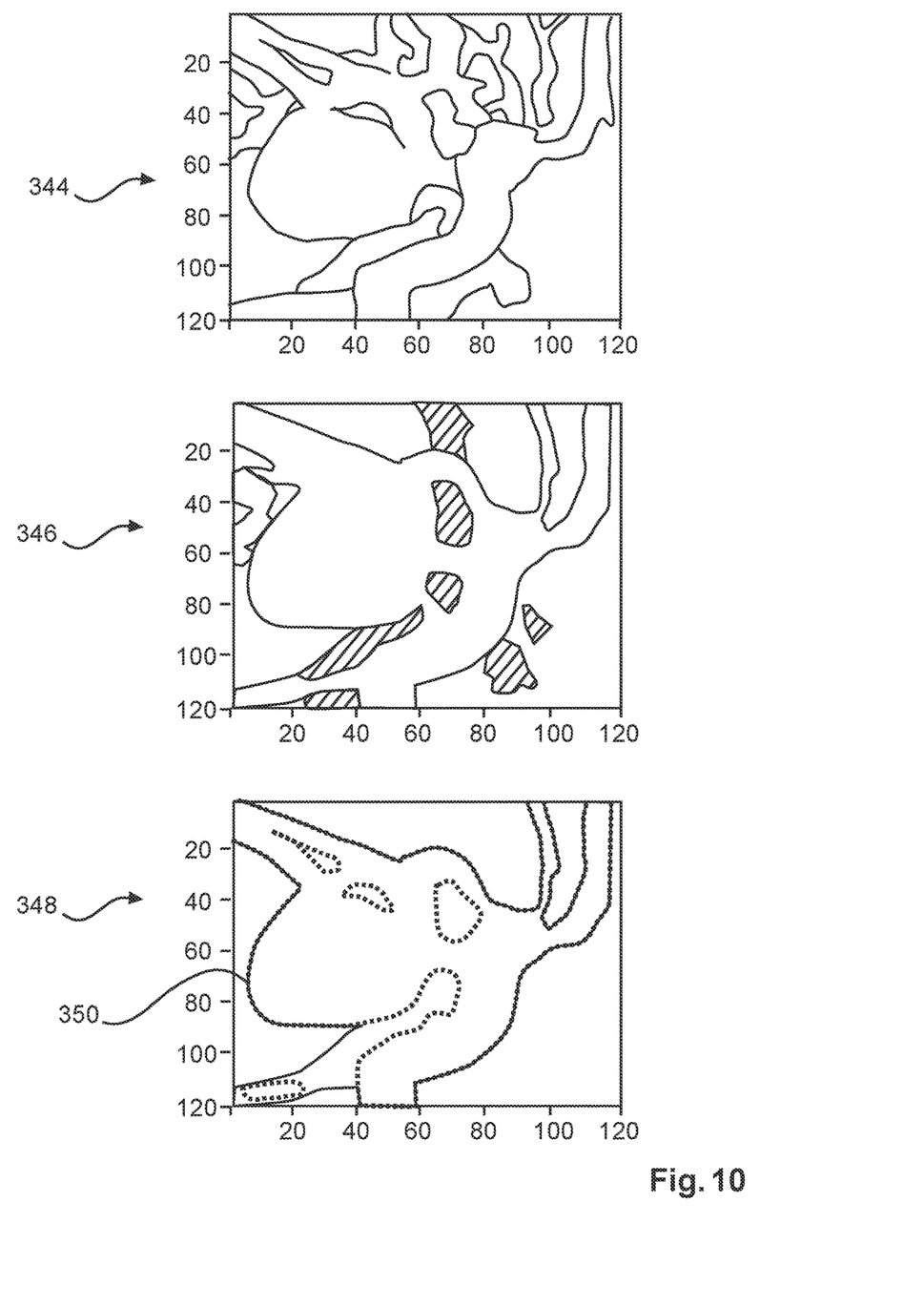
FIG. 10 shows a vessel confidence map, a contrast arrival time map and a connectivity map with segmentation outlines according to an example.

For illustration purposes, FIG. 10 shows a graphical representation of the above-mentioned vessel confidence 344 in the upper part and a contrast arrival time representation 346 in the middle part. In the representation of the vessel confidence 344, the vessel confidence may be indicated using a greyscale, where white pixels indicate high vessel confidence and dark pixels indicate low vessel confidence. In the contrast arrival time representation 346, the arrival time may be indicated using a rainbow colour-scale, ranging from blue, via green and yellow to red where blue indicates early contrast arrival and red indicates late contrast arrival. Further, in the lower part, a segmentation representation 348 is indicating the connectivity. For example, the time resolution can be provided also with higher resolution, which would thus lead to more precise segmentation information. The segmentation representation 348 is shown with an outline 350 that can be used as input for further algorithms, showing connected vessels, for example for calculating blood flow. The outline 350 can also be provided for further manual correction.

Figure 11:
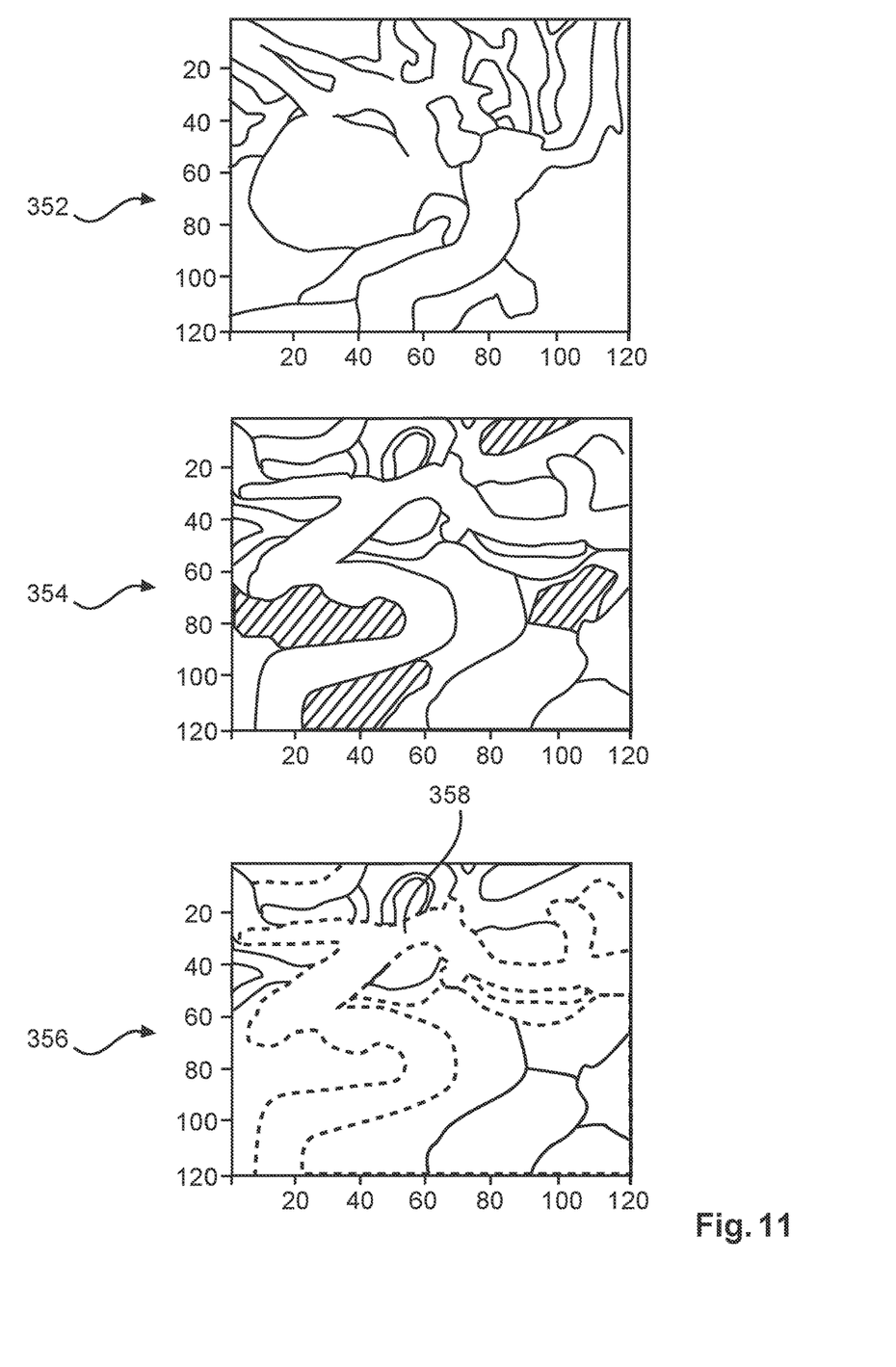
FIG. 11 shows a vessel confidence map, a contrast arrival time map, and a connectivity map of a further example.

FIG. 11 shows a further example of a vessel confidence representation 352 in the upper part, a contrast arrival time representation 354 in the middle part, and a segmentation representation 356 in the lower part, also with an outline 358. The vessel confidence representation 352 indicates vessel structures revealed by the contrast injection during the sequence acquisition. It contains many vessels, and many overlapping vessel segments. The contrast arrival time representation 354 indicates when the wash in contrast wave front reaches each point of the arterial structure. Early arrivals may be provided in blue, late arrivals in red. Higher gradients of this image indicate discontinuity of the contrast path in the structure, allowing to get the segmentation representation 356. This segmentation representation 356 provides a vessel structure temporally connected, corresponding to the spatially connected structure.

Figure 12:
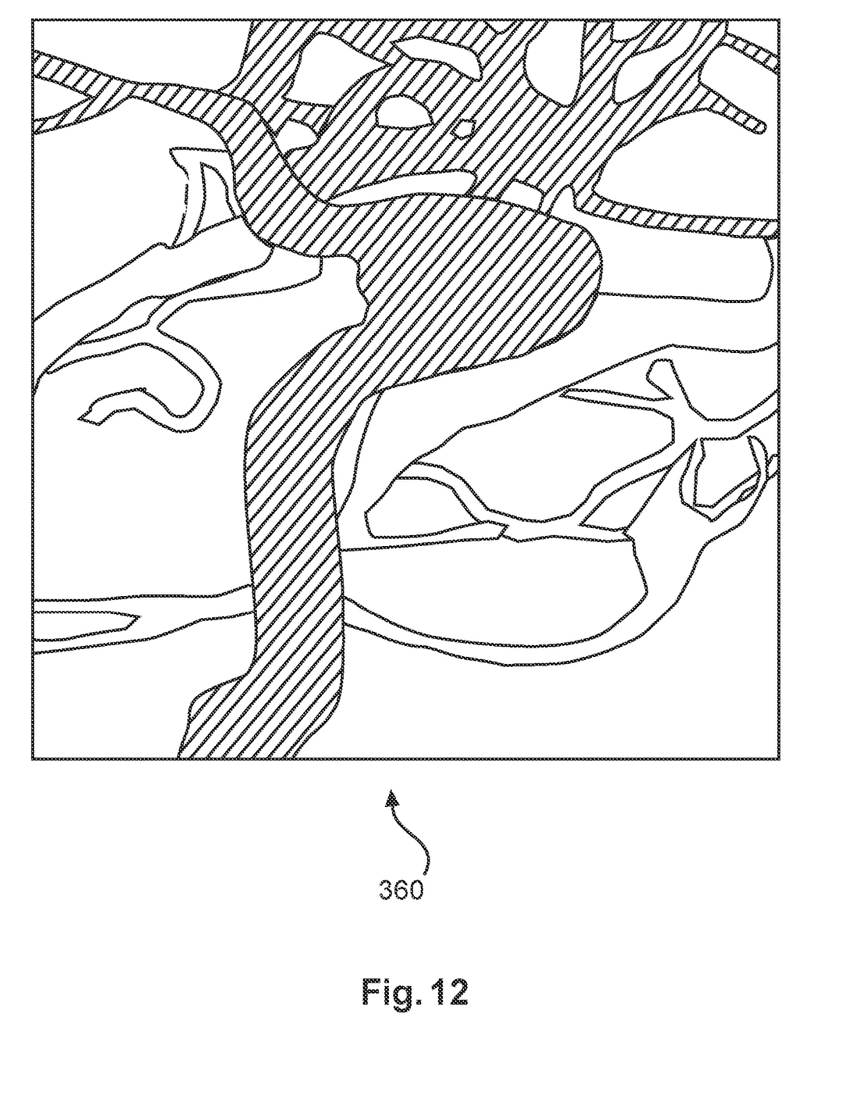
FIG. 12 shows an example of a contrast progression map.
Figure 13:
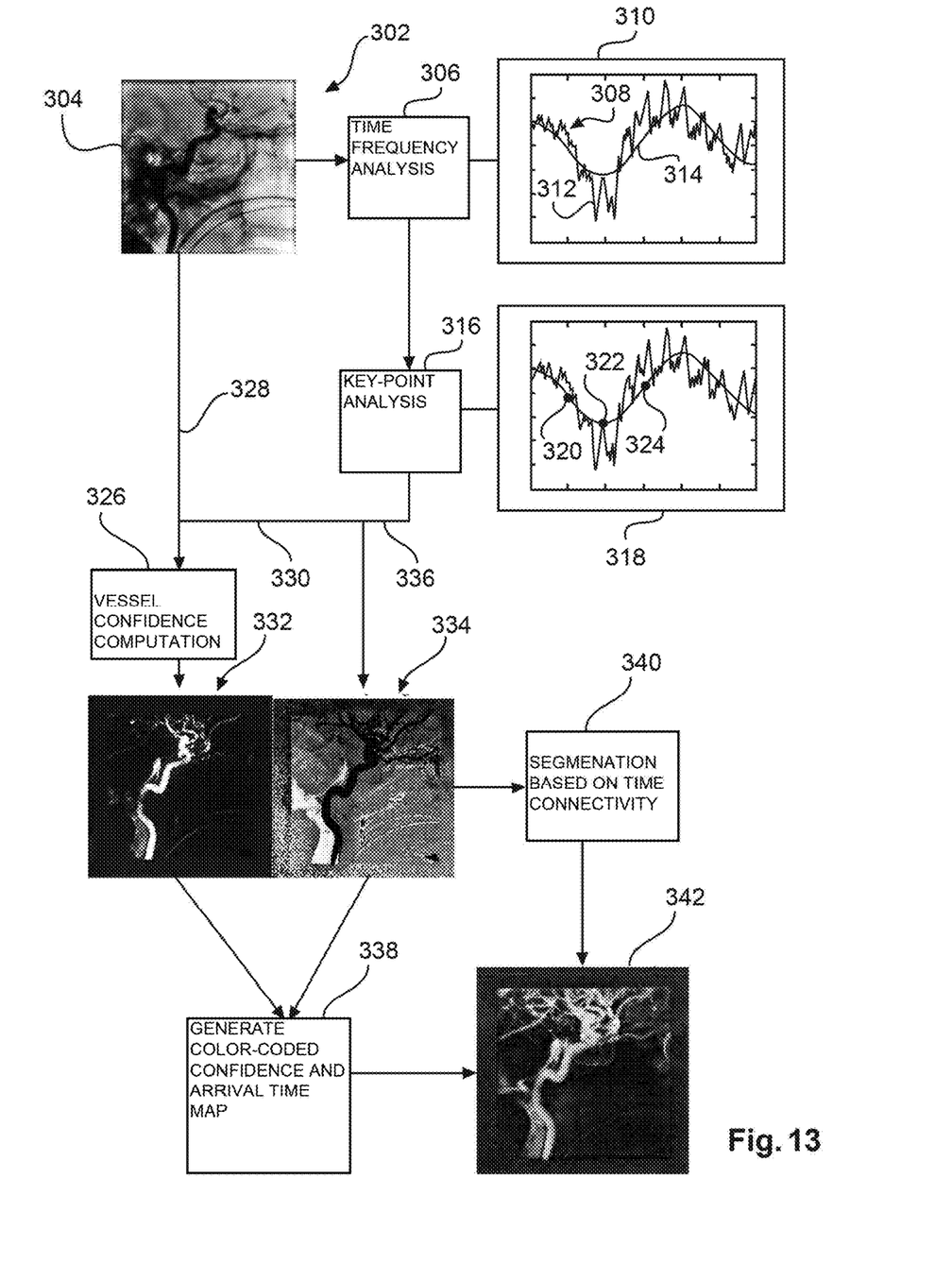
FIGS. 13, 14, 15 and 16 show graphical representations with photographic illustrations of the examples shown in FIGS. 9, 10, 11 and 12.
Figure 14:
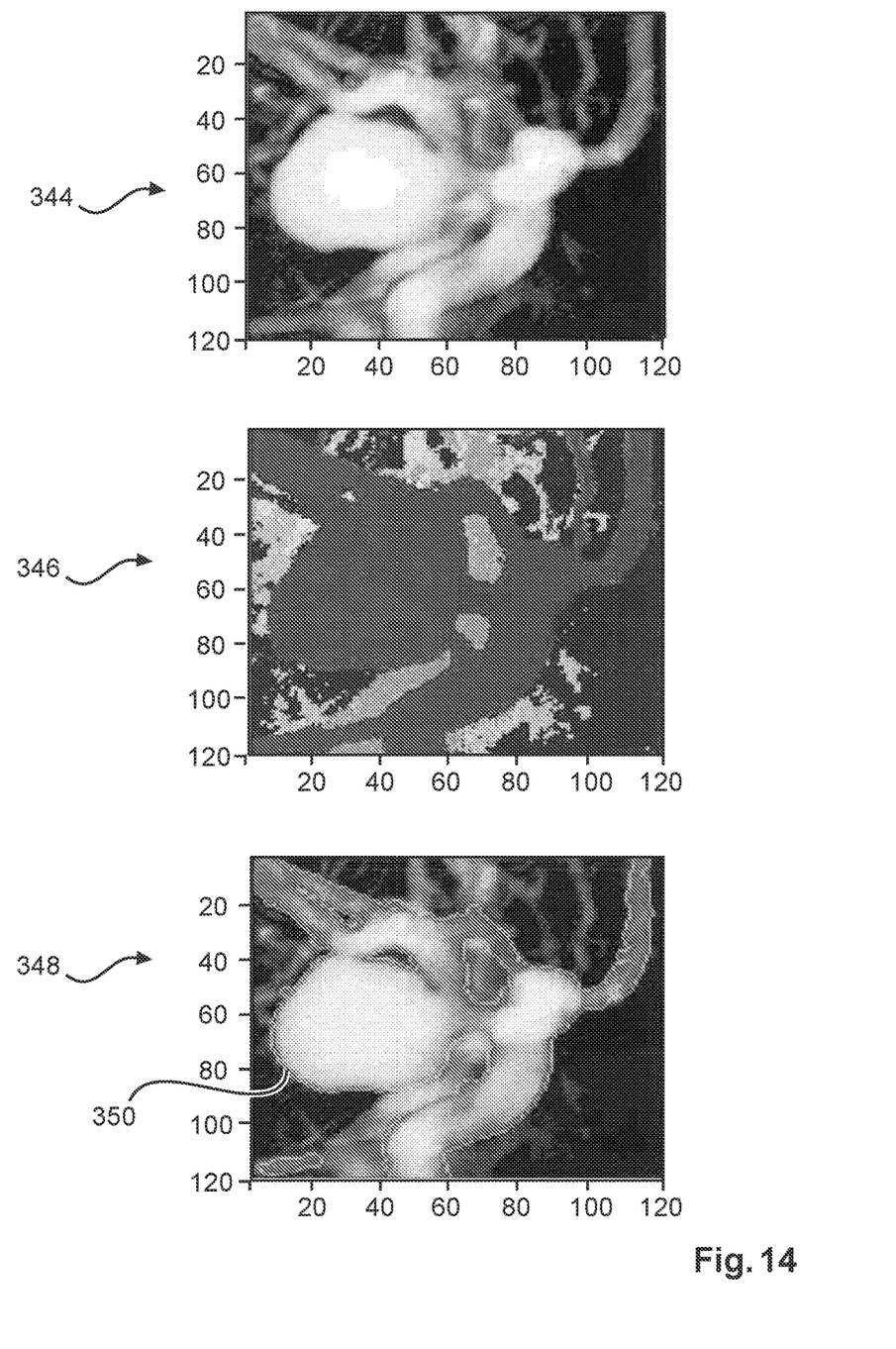
Figure 15:
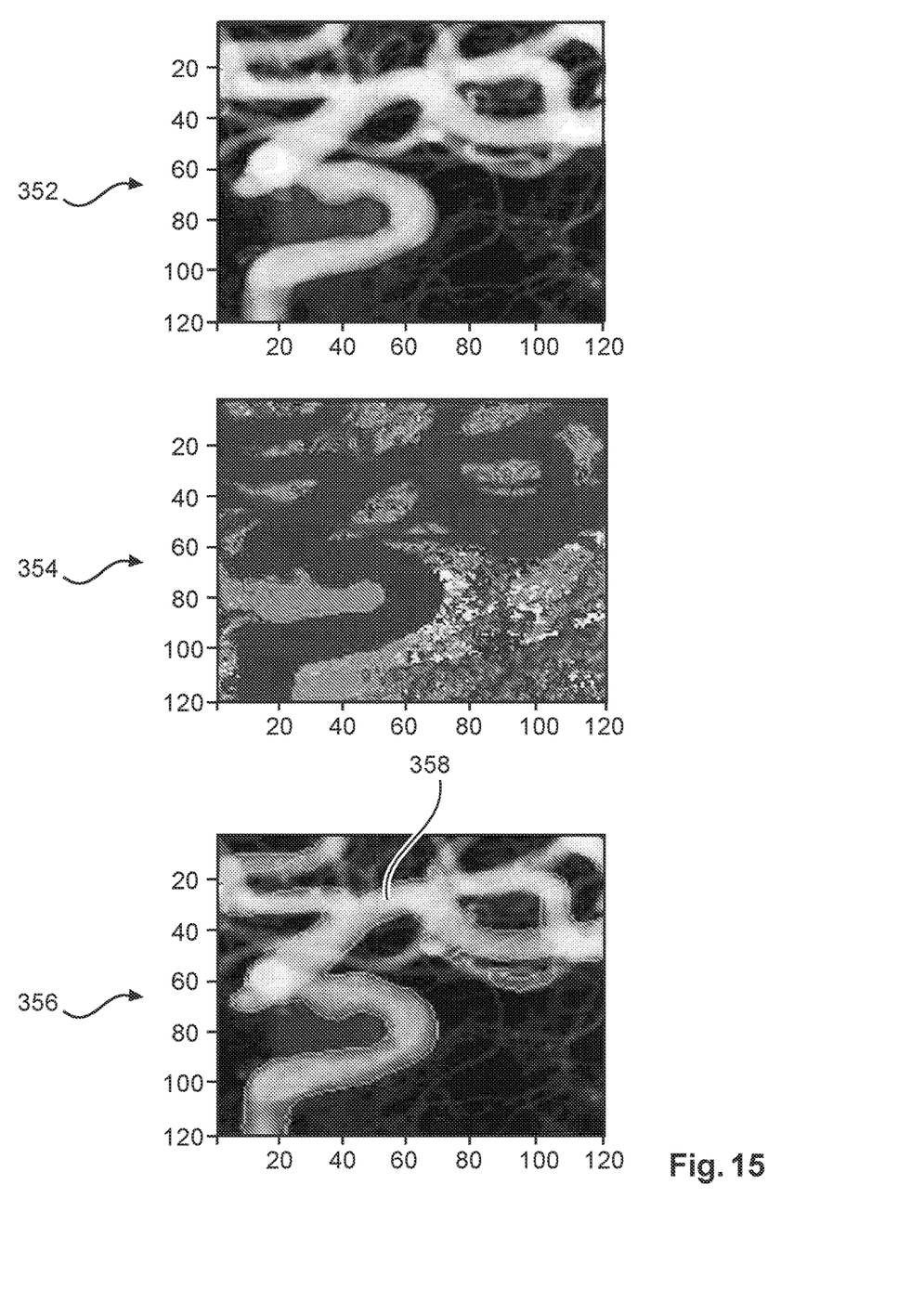
Figure 16:
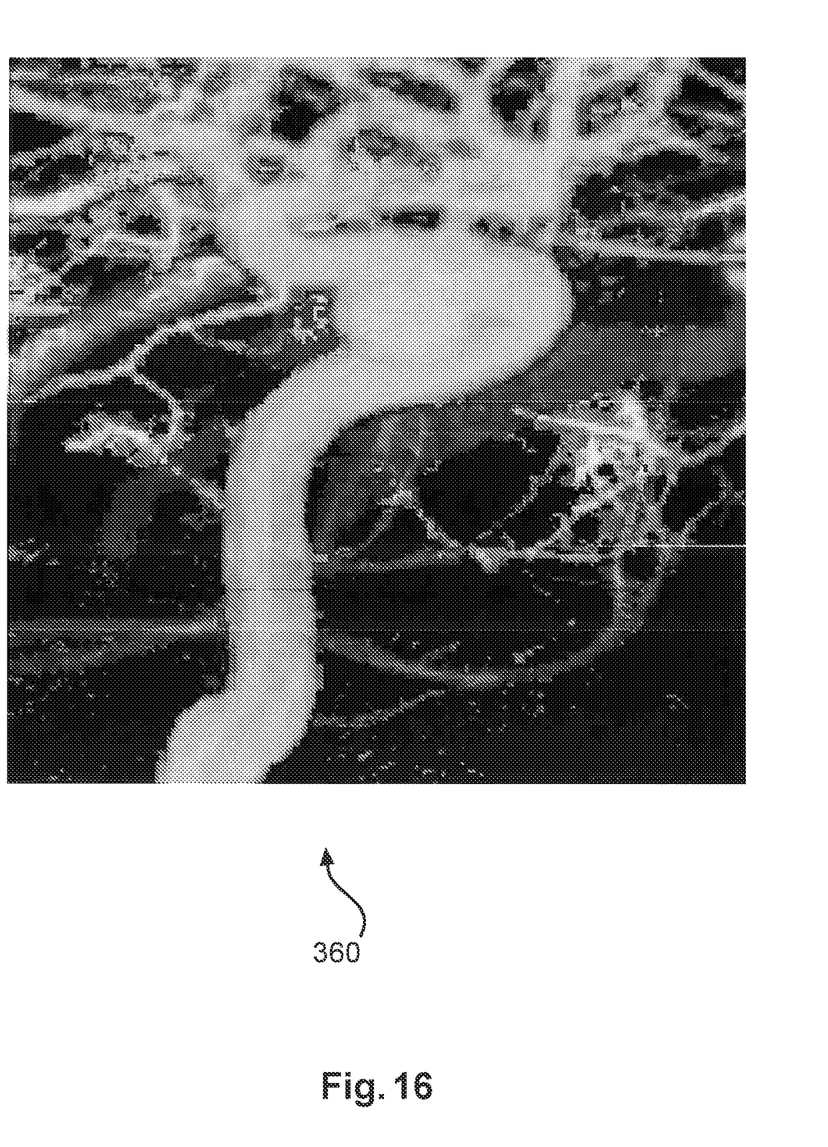

FIG. 12 shows an example of a contrast progression map 360, where depth information is provided visually to the user, but also to further calculation steps, for example for calculating blood flow.

According to an aspect, a 2D image analysis method with the basic aspects of vessel confidence, time arrival map, and spatial difference (pixel intensity) combined with temporal difference is provided for achieving segmentation. According to a further example, the procedure can be further refined by taking into account a spatial and temporal gradient of the image sequence, to create an image where overlapping structures are well separated. This image consists in merging information from the vessel confidence map, the estimated arrival time and additional information containing the absolute squared difference between time sequences of neighboured pixels. When the squared differences are higher than a certain criterion, e.g. a fixed threshold, or the local flow velocity that has been calculated per pixel, they are considered not to be connected. Such image is shown in FIG. 12.

As an advantage it must be noted that when a vessel crosses in background, then the connectivity information stored in the pixels will indicate that there is no connection between the foreground vessel and the background vessels, even though their pixels are direct neighbours. It is possible to use the connectivity information to refine the flow calculations. Blood can only flow through pixels that are connected. Moreover, this procedure creates a 3D visual effect that simplifies the delineation of complex overlapping structures.

The procedure can also be extended to detect for every pixel multiple contrast arrival times in the event of overlapping vessels. This information can be used to store connectivity in multiple layers, so that for each pixel, the connectivity is stored for each vessel segment separately. The multi-layer connectivity can then be used to separate the contrast wave in different layers, and repeat that flow calculation for each layer separately. For example, overlapping vessels are dissected in multiple layers. The flow wave can then be followed for each layer separately, i.e. a vessel in the foreground is shown on one layer and a vessel behind is shown on a second layer, wherein both layers cane be presented separately, e.g. displaced from each other.

FIGS. 13 to 16 show examples of FIGS. 9 to 12, where instead of graphical line representations, photographical images are inserted, but in relation with the same reference numerals. These further figures are provided for better understanding and need no further explanation.

In another exemplary embodiment of the present invention, a computer program or a computer program element is provided that is characterized by being adapted to execute the method steps of the method according to one of the preceding embodiments, on an appropriate system. The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention. Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid state medium supplied together with or as part of other hardware, but may also be distributed in other forms, such as via the interne or other wired or wireless telecommunication systems. However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray image processing device, comprising:
   a memory;
   an input; and
   a processor coupled to the input and the memory, wherein the memory configures the processor to receive from the input a sequence of time series angiographic 2D images of a vascular structure obtained along a given viewing angle and after a contrast agent injection with only one 2D image for each point in time and each of the time series of 2D images being obtained along the given viewing angle;
   wherein the processor is further configured to determine from the time series of 2D images, an arrival time index of a predetermined characteristic related to the contrast agent injection for each of a plurality of pixels along the time series of 2D images; to compute a connectivity index for each of the plurality of pixels in the 2D images based on the arrival time index; and to generate segmentation data of the vascular structure including segmentation of touching and overlapping vascular structure from the plurality of pixels in the 2D images wherein false connections of the touching and overlapping vascular structure are removed, wherein the segmentation data is based on the connectivity index of the plurality of pixels in the 2D images; and to provide the segmentation data for further purposes.

2. The X-ray image processing device according to claim 1, wherein the processor is further configured to compute a vessel confidence index for each of the plurality of pixels in the 2D images; and to compute the connectivity index for each of the plurality of pixels in the 2D images by combining the vessel confidence index with the arrival time index.

3. The X-ray image processing device according to claim 1, comprising:
   a display unit coupled to the processor;
   wherein the processor is further configured to generate a segmentation outline of the vascular structure from the segmentation data; and
   wherein the display unit is configured to display the segmentation outline.

4. An X-ray imaging system, comprising:
   the X-ray image processing device according to claim 1;
   an X-ray imaging device, wherein the processor is coupled to the X-ray imaging device;
   wherein the X-ray imaging device is configured to generate a sequence of time series angiographic 2D images of a vascular structure with only one 2D image for each point in time.

5. The X-ray imaging system according to claim 4, comprising:
   an injection device;
   wherein the injection device is configured to controllably inject contrast agent into a vascular structure of an object while the processor receives the sequence of time series 2D images.

6. A method for providing segmentation information, comprising acts of:
   a1) providing a sequence of time series angiographic 2D images of a vascular structure obtained along a given viewing angle and after a contrast agent injection with only one 2D image for each point in time and each of the time series of 2D images being obtained along the given viewing angle;
   b1) determining from the time series of 2D images, an arrival time index of a predetermined characteristic related to the contrast agent injection for each of a plurality of pixels in the 2D images along the time series;
   c) computing a connectivity index for each of the plurality of pixels in the 2D images based on the arrival time index;
   d) generating segmentation data of the vascular structure including segmentation of touching and overlapping vascular structure from the plurality of pixels in the 2D images wherein false connections of the touching and overlapping vascular structure are removed, wherein the segmentation data is based on the connectivity index of the pixels; and e) providing the segmentation data for further purposes.

7. The method according to claim 6, wherein it is provided:
b2) computing a vessel confidence index for each of the plurality of pixels in the 2D images; and
c) comprises computing the connectivity index for each of the plurality of pixels in the 2D images combining the vessel confidence index with the arrival time index.

8. The method according to claim 6, wherein following act a1), further comprising acts of:
a2) computing a time-frequency analysis for providing a sequence of filtered images; and
act b1) and/or act b2) are based on the filtered images.

9. The method according to claim 6, wherein for generating the segmentation data in act d), adjacent pixels are compared, and pixels in the 2D images are considered as connected if:
i) a difference between the values of their contrast arrival time index is smaller than a predetermined threshold; and/or
ii) the values of their vessel confidence index are higher than a predetermined threshold.

10. The method according to claim 6, wherein act e) comprises an act of generating a segmentation outline of the vascular structure from the segmentation data; and
wherein it is provided:
f) displaying the segmentation outline.

11. The method according to claim 10, wherein act f) comprises an act of superposing the segmentation outline onto a composite image generated from the vessel confidence index and the arrival time index of the pixels providing a contrast progression map to a user.

12. The method according to claim 6, wherein for overlapping vessels, at least two arrival time indices are determined; and wherein at least two connectivity indices are determined and stored separately.

13. The method according to claim 6, wherein following act d), comprising an act of using the connectivity information comprised in the segmentation data as a mask in a following flow algorithm for determining blood flow information.

14. A computer program element stored on a non-transitory computer readable memory for controlling a device according to claim 1, which, when being executed by a processing unit, is adapted to perform the method acts.

15. A non-transitory computer readable medium having stored the program element of claim 14.

* * * * *